United States Patent
Stein et al.

(10) Patent No.: US 10,898,606 B2
(45) Date of Patent: Jan. 26, 2021

(54) SELF-FUSING LOW DENSITY SILICONE

(71) Applicant: Legacy Research and Development Group, LLC, New Philadelphia, OH (US)

(72) Inventors: Michael E. Stein, New Philadelphia, OH (US); Sean Dickson, Marietta, GA (US)

(*) Notice: Subject to any disclaimer, the term of this patent is extended or adjusted under 35 U.S.C. 154(b) by 5 days.

(21) Appl. No.: 16/412,740

(22) Filed: May 15, 2019

(65) Prior Publication Data

US 2019/0351093 A1 Nov. 21, 2019

Related U.S. Application Data

(60) Provisional application No. 62/671,584, filed on May 15, 2018.

(51) Int. Cl.

| C08L 83/04 | (2006.01) |
|---|---|
| A61L 15/58 | (2006.01) |
| A61F 13/02 | (2006.01) |
| A61L 15/42 | (2006.01) |
| C08J 9/00 | (2006.01) |
| A61F 13/00 | (2006.01) |
| C08G 77/20 | (2006.01) |

(52) U.S. Cl.
CPC ........ *A61L 15/585* (2013.01); *A61F 13/0206* (2013.01); *A61F 13/0253* (2013.01); *A61F 13/0273* (2013.01); *A61L 15/425* (2013.01); *C08J 9/0061* (2013.01); *C08J 9/0066* (2013.01); *C08L 83/04* (2013.01); *A61F 2013/00153* (2013.01); *A61F 2013/00217* (2013.01); *C08G 77/20* (2013.01); *C08J 2383/07* (2013.01); *C08J 2483/04* (2013.01); *C08L 2205/025* (2013.01)

(58) Field of Classification Search
CPC .. A61L 15/585; A61L 15/425; A61F 13/0253; A61F 13/0206; A61F 13/0273; A61F 2013/00153; A61F 2013/00217; C08J 9/0066; C08J 9/0061; C08J 2483/04; C08J 2383/07; C08L 83/04; C08L 2205/05; C08G 77/20
See application file for complete search history.

(56) References Cited

U.S. PATENT DOCUMENTS

| 3,006,463 | A | 10/1961 | Bond et al. |
|---|---|---|---|
| 3,059,764 | A | 10/1962 | Tomita et al. |
| 3,943,091 | A | 3/1976 | Akiyama |
| 5,545,397 | A * | 8/1996 | Spielvogel ......... A61K 49/0433 |
| | | | 424/9.4 |
| 5,807,507 | A | 9/1998 | Hirano et al. |
| 5,939,339 | A | 8/1999 | Delmore et al. |
| 6,346,556 | B2 | 2/2002 | Baba et al. |
| 8,034,430 | B2 | 10/2011 | Efremova et al. |
| 8,142,382 | B2 | 3/2012 | Vito et al. |
| 9,327,098 | B2 | 5/2016 | Kelvered et al. |
| 2001/0044479 | A1 | 11/2001 | Baba et al. |
| 2004/0121683 | A1 | 6/2004 | Jordan et al. |
| 2008/0214688 | A1 | 9/2008 | Hirabayashi et al. |
| 2011/0067799 | A1 | 3/2011 | Mussig et al. |
| 2013/0178348 | A1 | 7/2013 | Nakajima et al. |
| 2014/0018717 | A1 | 1/2014 | Dillon |
| 2014/0303541 | A1 | 10/2014 | Vachon |
| 2015/0343750 | A1 | 12/2015 | Liu et al. |
| 2016/0296655 | A1 | 10/2016 | Suschek |
| 2017/0029623 | A1 | 2/2017 | Wang et al. |
| 2017/0102337 | A1 | 4/2017 | Benson et al. |

FOREIGN PATENT DOCUMENTS

| EP | 3259307 B1 | 8/2016 | |
|---|---|---|---|
| WO | 2012050448 A1 | 4/2012 | |
| WO | 2015013093 A1 | 1/2015 | |
| WO | 2016141450 A1 | 9/2016 | |
| WO | WO-2017086791 A1 * | 5/2017 | ......... A61L 24/0089 |
| WO | 2018108693 A1 | 6/2018 | |

* cited by examiner

*Primary Examiner* — Ali Soroush
(74) *Attorney, Agent, or Firm* — Black, McCuskey, Souers & Arbaugh LPA

(57) ABSTRACT

An adhesive free self-fusing material being either of open or closed cell polymer (silicone) based material that can be used to create a permanent elastic band for compression and support dressings. The proprietary polymer material upon contact with itself, initiates a "room temperature" reaction of self-vulcanization with the contact surfaces of itself. This eliminates the need for any adhesives which some patients experience negative reactions. In an example embodiment, the material comprises Vinyl stopped polydimethyl siloxane, amorphous silica, and dimethylpolysiloxane.

11 Claims, 1 Drawing Sheet

SELF-FUSING LOW DENSITY SILICONE

CROSS REFERENCE TO RELATED APPLICATIONS

This application claims the benefit under 35 U.S.C. § 119 of U.S. Provisional Application No. 62/671,584 filed May 15, 2018.

TECHNICAL FIELD

The present disclosure relates generally to a self-fusing silicone sponge tape that is useful in field dressings, and in particular to an adhesive free, self-fusing polymer elastic bandage/wrap for compression and support systems/structures for medical purposes.

BACKGROUND

Adhesive bandages are used to protect wounds from friction, bacteria, damage and dirt in order to facilitate the healing process. Typically, an adhesive bandage lays flat on the wounds and is covered by a woven plastic or latex strip that contains an absorbent dressing that may or may not be medicated with an antibacterial or antiseptic compound. The bandage is usually applied such that the dressing covers the wound and the woven plastic or latex strip is adhered to the skin thereby holding the bandage in place over the wound.

BRIEF DESCRIPTION OF THE DRAWINGS

The accompanying drawings incorporated herein and forming a part of the specification illustrate the example embodiments.

SUMMARY OF EXAMPLE EMBODIMENTS

Figure 1:
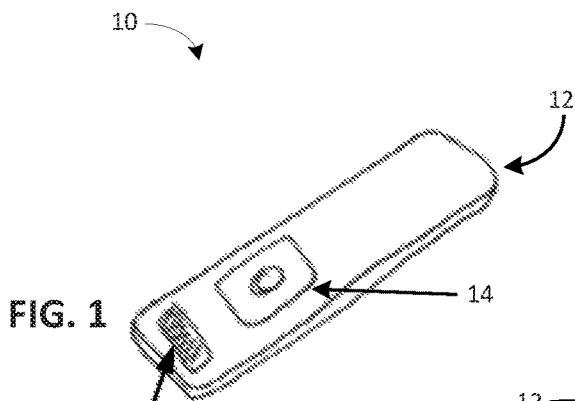
FIG. 1 illustrates an example of a bottom of a self-fusing bandage in accordance with an example embodiment.

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In accordance with an example embodiment, there is disclosed herein, a self-fusing, or self-amalgamating tape, wherein the tape is a low-density tack-free tape which, when wrapped to itself, fuses into a uniform construction. In an example embodiment, the tape is used as a self-fusing bandage as will be described herein.

DESCRIPTION OF EXAMPLE EMBODIMENTS

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

Described in an example embodiment herein is a tape made of a material that will be further described herein (e.g., a Low Density Self-Fusing Silicone rubber—Open or Closed Cell, which may also be referred to herein as a "sponge" or "foam") that can be employed, inter alia, as a self-fusing bandage. The tape is suitable for use as a battlefield/trauma dressing. For example, the self-fusing bandage can be wrapped tightly and will maintain the applied pressure against the wound and not just slide since the material employed in the bandage is self-fusing. An aspect of this example embodiment is that it can enable the elimination of adhesives or glues which can cause an allergic reaction upon contact with the skin.

In another example embodiment, the material can be employed as a flexible cast. For example, the tape can be used to wrap a sprained ankle or wrist. Unlike cloth materials which can absorb water, blood, or other liquids, which can also stretch and not stay on the wound, the material described in an example embodiment herein would prevent a wound from getting wet and lose any of its properties when exposed to liquids. In particular embodiments, holes or vents can be incorporated into the material to allow the material to breathe.

In an example embodiment, the (Low Density Self-Fusing Silicone rubber—Open or Closed Cell) material is comprised of the following materials:

| | |
|---|---|
| Vinyl stopped polydimethyl siloxane | 65-73% |
| Amorphous Silica | 20-34% |
| Dimethylpolysiloxane | 1-7% |
| Blowing Agent (AIBN or industry standard equivalent) | 1-15% |
| Boron additive | 1-5% |
| Curing Agents: peroxides, or polyaddition | 1-5% |
| Pigment: Organic or Inorganic | 1-5% |

In an example embodiment, the material is a heat curable silicone rubber composition curable through the use of peroxides, or polyaddition cure, systems known for use in silicone, and non-silicone, rubber technologies which is able to self-fuse without the aid of secondary or tertiary adhesives by employing the use of boron additives known for use in self-adhering or fusible tape silicone, and non-silicone, rubber technologies while providing a low density open, or closed, cell sponge system resulting in the vulcanized silicone rubber providing specific gravities in the range from 00.30 g/cc to 1.00 g/cc through the use of blowing agents known for use in silicone, and non-silicone, rubber technologies in any number of colors through the use of pigments known for use in silicone, and non-silicone, rubber technologies.

This new self-fusing, or self-amalgamating tape, is a low-density tack-free tape which, when wrapped to itself, fuses into a uniform construction. The tape can create an elastic structure or semi-rigid structure. The tape does not rely on secondary, or tertiary, adhesives as it is a self-fusing system. (Adhesive Free, no skin irritation or reactions). Adhesion only takes place when the silicone rubber tape comes into direct contact to itself. It is at that point chemical bonds form to produce the fusing/amalgamation. The unique application of self-fusing tapes is the ability to wrap irregular geometries for the purpose of joining, sealing, and insulating. All known forms of this technology are currently supplied in a dense form ranging from a 1.16 to 1.20 g/cc specific gravity with a Shore A durometer of 50 to 65. What makes the tape described in an example embodiment herein unique is that it is a low-density system ranging from a 0.55 to 1.00 g/cc specific gravity which results in a 50% reduction in volumetric weight with a Shore A durometer of 15-45. In addition, due to the lower density, the tape is less thermally conductive thereby reducing thermal transmission of heat. This can be useful for shielding IR signatures.

FIG. 1 illustrates an example of a bottom of a self-fusing bandage 10 in accordance with an example embodiment. The bandage 10 comprises a tape 12 made of the material described herein. In an example embodiment, the bandage 10 comprises an optional built-in wound pressure and/or absorbent patch 14. In another example embodiment, the bandage comprises an optional starter adhesive strip 16 to adhere to the skin at the start of wrapping. In particular embodiments, the bandage may comprise both a starter adhesive and a wound pressure and/or absorbent patch.

Figure 2:
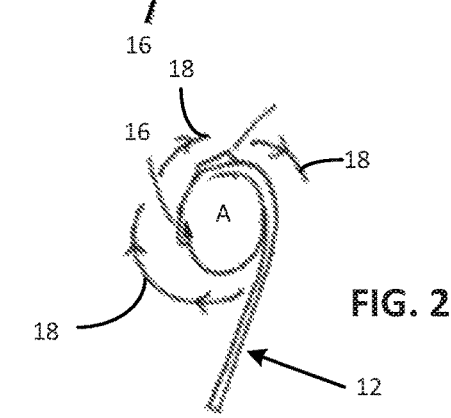
FIG. 2 illustrates an example of the self-fusing bandage being wrapped around a limb.

FIG. 2 illustrates an example of the self-fusing bandage 10 being wrapped around an appendage A in the direction indicated by arrows 18. As those skilled in the art can readily appreciate, the appendage A can be a limb such as an arm or leg, or any other part of a body such as the abdomen or head. The material is wrapped around the appendage a plurality of times forming a plurality of layers. The first layer is in contact with the patient's skin or substance on top of the skin such as clothing. The second and subsequent layers bond with the previous layer. For example, the second layer would bond with the first layer, the third layer with the second layer, etc. The bandage 10 may be wrapped around the appendage any number of times and is only limited by the amount of material available.

Figure 3:
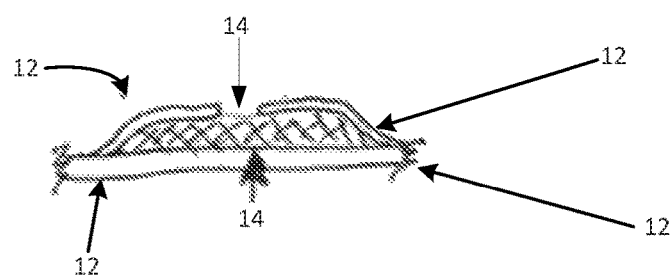
FIG. 3 illustrates an example cross section of a self-fusing bandage near the wound.

FIG. 3 illustrates an example cross section of a self-fusing bandage 10 near the wound. The bandage 10 comprises an optional built-in wound pressure and/or absorbent patch 14 that covers the wound and a skin seal that fuses with the self-fusing bandage.

Figure 4:
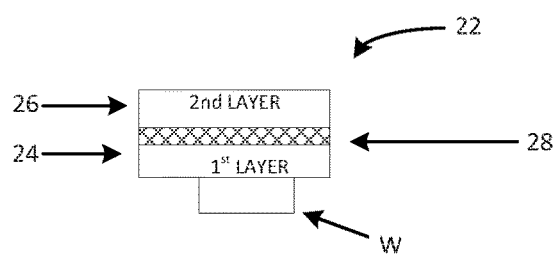
FIG. 4 illustrates another example cross sectional area of a self-fusing bandage near the wound that has a plurality of layers of the self-fusing bandage covering a wound.

FIG. 4 illustrates another example cross sectional area 22 of a self-fusing bandage near the wound W that has a plurality of layers of the self-fusing bandage covering a wound. In the illustrated example, a first layer (Layer 1) 24 of the bandage is in contact with the appendage and covers the wound W and as in contact with the appendage (e.g., the skin around the wound and/or clothing or other material on top of the skin, not shown, see e.g., A in FIG. 2). As the bandage is wrapped around the appendage a second layer (Layer 2) 26 of the material covers the first layer. The material of the first and second layers 24, 26 bond, or fuse, together. Once the bond 28 is formed, the material will not loosen. As those skilled in the art can readily appreciate, any physically realizable number of layers may be added to the top of dressing. The only limitation is the amount of material that is available.

As those skilled in the art can readily appreciate, the material described herein employed for tape 12 can be manufactured in any length, width, shape or profile and still retain the self-vulcanizing/contact bond features. The material can be infused with anti-microbial organic and inorganic compounds 'active ingredients' to hinder or reduce bacterial/viral growth. The material will not absorb blood or other bodily and environmental contaminates like traditional cloth bandages due to its cellular structure. Besides bandage/ wound care, an example embedment described herein can be used to create a support system such where a wrist, ankle or foot needs wrapped to prevent movement. This will create a "one piece" support wrap which will hold its placement and will not become contaminated from external sources. As those skilled in the art will further appreciate, this material 12 eliminates the need for adhesives which can cause irritation when put into contact with the skin since the material 12 bonds to itself adhesive free, and thus eliminates the problems that can be caused by adhesives. For example, once the bond 28 is formed, the material will not loosen.

As those skilled in the art can readily appreciate, although the self-fusing silicon rubber tape/foam has described herein for use as a bandage, there are many other additional uses for the self-fusing silicon rubber, including but not limited to industrial, commercial, military, and firearms/hunting. For example, industrial uses include, but are not limited to wraps for exhausts/mufflers, combustion motor wraps, wiring, fuel lines, grips for hand tools, power tools, custom gaskets, wiring wrap, grip handles, plumbing pipe insulation, window and door seals—with the ability to create custom fusible lengths without needing to do splice molding or gluing operations. Examples of commercial uses include, but are not limited to golf club handles, bicycle grips, fishing net handles, fishing reels and poles, cooking utensils and handles, or any implement or device used for hitting a ball in a sporting event—golf club, racquets, hockey sticks, bats, and/or lacrosse grips, etc. Examples of military use include but are not limited to any type of heat/abrasion wrap for thermal mitigation or Infrared masking used on vehicles, aircraft, watercraft, weapons systems and/or EMF (Electromagnetic Field) shielding. Example uses with firearms/hunting include, but are not limited to thermal wraps for barrels, suppressors, hand grips, forend grips, slings, bow/cross bow grips, scope covers, hunting stand wraps for around metal, ski poles, walking grips, wading grips, fishing pole wrap for handles for both grip and as a flotation aid.

As those skilled in the art can readily appreciate, the composition described herein can be made in any color, size, shape, profile, length. In an example embodiment, the composition may be reinforced. For example, a filament, roving, or solid silicone multilayer construction can provide enhanced mechanical properties.

In accordance with an example embodiment, the self-amalgamating low-density silicone sponge tape described herein under ordinary hand tension can be easily be stretched to at least twice its initial length and, upon release of stress, will retract substantially immediately to its original length. The self-amalgamating low-density silicone sponge tape is only slightly tacky and is easily handled with the fingers; yet it adheres to itself when overlapped upon itself. When the self-amalgamating low-density silicone sponge tape is stretched up to about twice its original length, under ordinary hand tension, and wrapped in convolutions upon itself around an object, it remains in place without unwinding even after an operator releases his fingers from the wrapping; and it becomes impossible to unwind or delaminate into its original tape form after it is left in such wrapped condition for a relatively short period of time at room temperature. In other words, after a period of time at room temperature it fuses together. It thus forms an integral, flexible, void-free seal. The seal has good electrical properties, thermal properties, resistant to ozone, buoyancy, deflection resistance, ultraviolet light resistance, moisture resistant, flame resistant, and thermal and electrical insulative properties over a wide temperature range of operation. For example, the composition can withstand continuous operation at 350 F. without embrittlement, cracking or appreciable loss of properties. It even can withstand short periods of operation at temperatures as high as 500 F. or higher. It further can withstand operation at temperatures as low as minus 80 F., or even lower, remaining suitably flexible and providing good mechanical and physical properties.

Described above are example embodiments. It is, of course, not possible to describe every conceivable combination of components or methodologies for purposes of describing the example embodiments, but one of ordinary skill in the art will recognize that many further combinations and permutations of the example embodiments are possible. Accordingly, it is intended to embrace all such alterations, modifications and variations that fall within the spirit and scope of any claims filed in applications claiming priority hereto interpreted in accordance with the breadth to which they are fairly, legally and equitably entitled.

The invention claimed is:

1. A self-fusing composition, comprising:
65-73% Vinyl stopped polydimethyl siloxane;
20-3% Amorphous Silica;
1-7% Dimethylpolysiloxane
1-15% blowing agent; and
1-5% Boron additive.

2. The composition according to claim 1, further comprising 1-5% curing agent.

3. The composition according to claim 2, wherein the curing agent comprises a peroxide.

4. The composition according to claim 2, wherein the curing agent comprises a polyaddition.

5. The composition according to claim 1, further comprising 1-5% pigment.

6. The composition of claim 5, wherein the pigment is organic.

7. The composition of claim 5, wherein the pigment is inorganic.

8. The composition of claim 1, wherein the composition is open cell.

9. The composition of claim 1, wherein the composition is closed cell.

10. The composition of claim 1, wherein the blowing agent is an effective amount to achieve a specific gravity of less than 1.0 g/cc.

11. The compound of claim 1, wherein the blowing agent is an effective amount to achieve a specific gravity in a range of 0.30 g/cc and 1.00 g/cc.

* * * * *

UNITED STATES PATENT AND TRADEMARK OFFICE
CERTIFICATE OF CORRECTION

| | | |
|---|---|---|
| PATENT NO. | : 10,898,606 B2 | Page 1 of 1 |
| APPLICATION NO. | : 16/412740 | |
| DATED | : January 26, 2021 | |
| INVENTOR(S) | : Michael E. Stein and Sean Dickson | |

It is certified that error appears in the above-identified patent and that said Letters Patent is hereby corrected as shown below:

In the Claims

Column 5, Line 22 Claim 1, "20-3% Amorphous Silica" should read --20-34% Amorphous Silica--.

Signed and Sealed this
Second Day of March, 2021

Drew Hirshfeld
*Performing the Functions and Duties of the
Under Secretary of Commerce for Intellectual Property and
Director of the United States Patent and Trademark Office*